United States Patent [19]
McFarland et al.

[11] Patent Number: 5,971,040
[45] Date of Patent: Oct. 26, 1999

[54] AUTOMATIC REFUELING LOGIC

[75] Inventors: James Ross McFarland; Jim Ross, both of Port Coquitlam, Canada

[73] Assignee: Shell Oil Company, Houston, Tex.

[21] Appl. No.: 09/070,261

[22] Filed: Apr. 30, 1998

Related U.S. Application Data

[60] Provisional application No. 60/045,131, Apr. 30, 1997.
[51] Int. Cl.[6] ..................................... B65B 1/04
[52] U.S. Cl. .............. 141/98; 141/392; 901/22; 901/41
[58] Field of Search .............. 141/98, 392, 94, 141/346, 348, 350; 901/22, 41, 16

[56] References Cited

U.S. PATENT DOCUMENTS

| | | | |
|---|---|---|---|
| 3,527,268 | 9/1970 | Ginsburgh | 141/98 |
| 4,913,613 | 4/1990 | Hirschmann | 901/22 |
| 5,098,024 | 3/1992 | MacIntyre et al. | 901/29 |
| 5,609,190 | 3/1997 | Anderson et al. | 141/98 |
| 5,758,701 | 7/1998 | Corfitsen | 141/98 |

FOREIGN PATENT DOCUMENTS

| | | | |
|---|---|---|---|
| 418 744 A2 | 3/1991 | European Pat. Off. | B60S 5/02 |
| WO 94/03391 | 2/1994 | WIPO | B67D 5/08 |

*Primary Examiner*—Steven O. Douglas
*Attorney, Agent, or Firm*—Del S. Christensen

[57] ABSTRACT

A system is disclosed for operating an automated refueling system, the system including: a source of vacuum; a suction cup, the suction cup being capable of mating with a hinged vehicle fuel cap cover and the suction cup having an inside which is in communication with the source of vacuum through a suction system; an extension mechanism effective to laterally extend the suction cup toward a vehicle's hinged fuel cap cover; a vacuum actuated means to swing open the hinged fuel cap cover when a pressure within the suction system approaches the pressure of the source of vacuum; and a vacuum actuated cylinder to extend a filler tube into fuel tank inlet after the hinged fuel cap door is swung open. The system of the present invention minimizes the number of electrical components that are in the vicinity of the refueling nozzle.

8 Claims, 3 Drawing Sheets

AUTOMATIC REFUELING LOGIC

This application claims the benefit of U.S. Provisional Application No. 60/045,131, filed Apr. 30, 1997, the entire disclosure of which is hereby incorporated by reference.

FIELD OF THE INVENTION

The invention relates to a logic system for controlling actions of an automated refueling system, and in another aspect, to an apparatus for opening a hinged cover.

BACKGROUND TO THE INVENTION

Numerous apparatuses have been proposed for automatic refueling of vehicles, but none have been commercially applied to retail gasoline outlets because of the expense and complexity of the systems. To be economically competitive with customers ability to refuel automobiles manually, or an attendant, such an automated refueling system must be relatively simple, and must be assembled from relatively inexpensive components. Additionally, it is necessary that modifications to the vehicle to be refueled be minimal. Also, the refueling nozzle area must be designed to be in an area that is free from the possibility of electrical sparks.

U.S. Pat. No. 3,527,268 suggests an automated refueling system that includes a movable head having three functional arms, an arm to open a fuel cap cover lid, an arm to remove a fuel cap, and a fuel fill nozzle that is inserted into the fuel inlet. There are therefore five physical steps used: fuel cap lid opening; cap removal; fuel fill step; cap replacement; and cap lid closure. The apparatus of '268 must be repositioned after each of these five operations. This repositioning adds to the complexity of any control scheme, adds to the time required to complete the operation, and results in an operation that would be perceived by the customer as unduly complex. Additionally, '268 initiates fuel flow upon the fuel tube being extended until a limit switch indicates it is fully extended. The initial positioning of the end effector must therefore be extremely accurate with relationship to the fuel inlet nozzle to provide any sort of seal on the fuel inlet. This precise of positioning with relationship to the fuel inlet nozzle is not possible because of variations in dimensions of fuel tank inlet tubes, variations in the installation of fuel tanks in vehicles, and variations in installation of fenders on the vehicles. Even if the position of the fuel inlet is determined by the position of the fuel cap, the angle of the fuel inlet orifice to vertical may vary sufficiently to prevent a seal being achieved at a predetermined fuel fill tube extension.

The apparatus of patent '268 reposition the end-effector for the different operations by rotation of the head of the end-effector. The connections and control conduits must therefore all be rotatable, and many require rotatable seals. This adds considerable cost and complexity to the apparatus of '268.

EPO Patent Publication No. 0 418 744 A2 suggests a robot that is mounted on a track adjacent to a stall in which a vehicle to be refueled is to be parked. In the apparatus of Publication '744, the robot picks up a selected refueling nozzle and inserts the nozzle into a specially provided insert in the vehicle's fuel inlet. Besides for the specially provided insert for the fuel inlet, the vehicle needed to be modified to provide the driver the capability of opening and closing the fuel inlet cover lid from the inside of the vehicle.

Patent PCT/IT/00017 suggests an automated refueling apparatus much like that of patent '268, but with a line of center of rotation turned 90° from the line of center of rotation of the fuel dispensing head. PCT/IT/00017 also suggests positions of the filling cover door and the fuel plug indicated by cameras searching for reflectors and fluorescent paint. Fuel flow is initiated when a sensor touches the fuel inlet, indicating that the fuel nozzle is inserted into the inlet. This mechanism would not necessarily indicate that a sealing contact is made.

It is therefore an object of the present invention to provide an apparatus for automated refueling of vehicles that is relatively simple and inexpensive. It is a further object to provide such a system wherein the electrical switches and sensors in the area around the refueling nozzle are minimized.

SUMMARY OF THE INVENTION

These and other objects are accomplished by a system for operating an automated refueling system, the system including: a source of vacuum; a suction cup, the suction cup being capable of mating with a hinged vehicle fuel cap cover and the suction cup having an inside which is in communication with the source of vacuum through a suction system; an extension mechanism effective to laterally extend the suction cup toward a vehicle's hinged fuel cap cover; a vacuum actuated means to swing open the hinged fuel cap cover when a pressure within the suction system approaches the pressure of the source of vacuum; and a vacuum actuated cylinder to extend a filler tube into fuel tank inlet after the hinged fuel cap door is swung open. This system is relatively simple and minimizes any need for sensors and control/sensing components. The system of the present invention also minimizes the number of electrical components that are in the vicinity of the refueling nozzle.

A pneumatic logic system can be used to trigger positive fluid pressure (preferably air pressure) cylinders to move the components of the system. Considerably smaller cylinders are required when positive fluid pressure is utilized rather than negative gauge pressures because high pressure cylinders are considerably smaller than vacuum actuated cylinders.

In another aspect the present invention relates to a J-shaped suction cup for pulling open the hinged cover by application of a vacuum to the inside of the suction cup.

DESCRIPTION OF A PREFERRED EMBODIMENT

The present invention utilizes a suction cup to attach to a hinged fuel inlet cover in order to pull open the fuel inlet cover in an automated refueling system. This suction cup is provided with a vacuum from a source of vacuum such as, for example, a vacuum pump or a venturi. The source of vacuum is in communication with the inside of the suction cup through a suction system. When this suction cup is not mated to a surface, pressure within the vacuum system is considerably greater (closer to zero gauge pressure) than the pressure of the source of the vacuum. When the suction cup is moved forward and mates with a flat surface, such as the fuel inlet cover, pressure within the suction cup (and the suction system) is drawn down to a negative pressure that is near the pressure of the source of the vacuum. This negative pressure within the suction system can either directly cause movement of the suction cup to pull open the fuel inlet cover (by way of an vacuum actuated cylinder), or act on a poppet valve to cause movement of the suction cup. After movement of the fuel inlet cover door is initiated, movement of a fuel filler tube toward the fuel inlet is initiated. Seating of the fuel filler tube in the fuel inlet preferably triggers opening of a fuel valve to initiate refueling.

Fueling can alternatively be initiated when mating of the fuel inlet with the filler tube is confirmed by, for example, a decrease in pressure in a vapor recovery system which removes hydrocarbon vapors from the fuel tank as fuel is inserted. An alternative method to initiate fueling, such as this, can also be incorporated as a redundant signal to increase reliability.

When a pneumatic signal is used to actuate the fuel valve, the fuel valve can optionally be located remote from the filler tube, although whether the trigger for the fuel filler tube is mechanical or pneumatic, the fuel valve is preferably located close to the filler tube.

Figure 1:
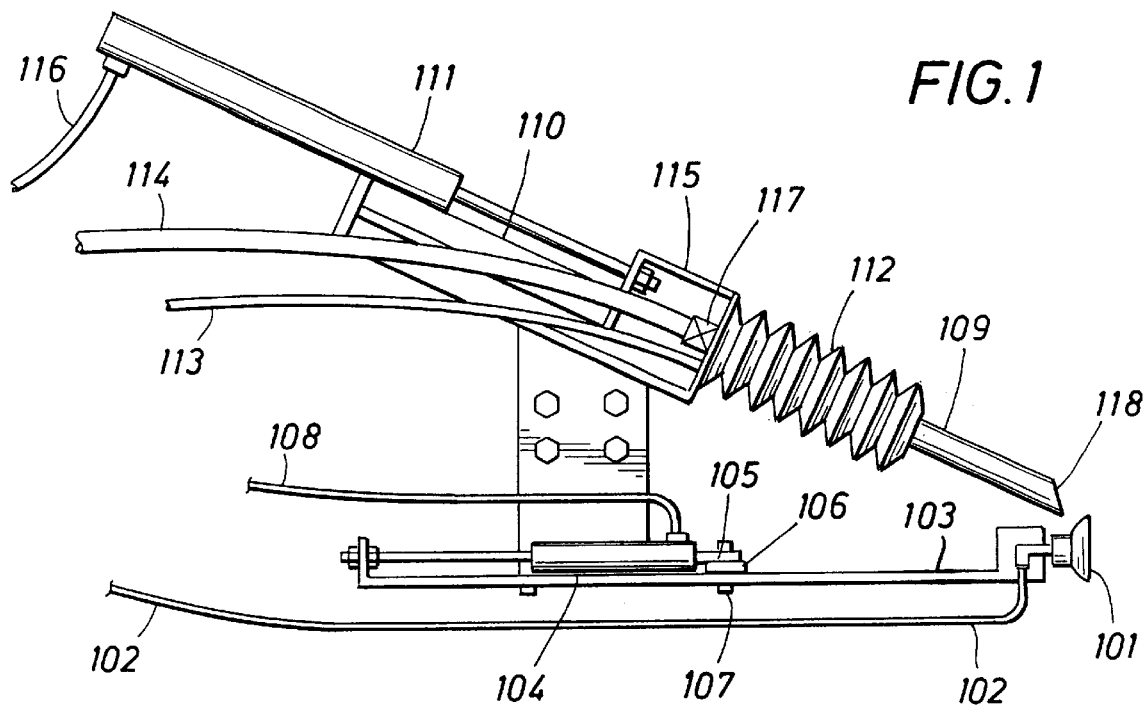
FIG. 1 is a schematic drawing of components of an embodiment of the present invention.

Referring now to FIG. 1, an arrangement of an end-effector effective for practice of the present invention is shown. A suction cup 101 is connected to a source of vacuum by a flexible tube 102, and is supported on an arm 103, which is capable of swinging open the fuel inlet cover. A pneumatic cylinder 104 provides movement of the suction cup in an arch around a hinge of the fuel cover door. A fixed end 105 of the pneumatic cylinder is attached to a support 106 by a bolt 107. The fixed end of the pneumatic cylinder preferably pivots around the bolt. Power for the pneumatic cylinder is shown to be by a air supply line 108 which comes from a poppet valve (not shown), the poppet valve being actuated by a lower pressure being sensed in the vacuum supply system, and when actuated, the poppet valve opening to supply pneumatic cylinder with air pressure. The support also provides a mounting for a fuel filler tube 109. The fuel filler tube is moved at an angle from horizontal into a fuel inlet of a vehicle. Movement of the filler tube is shown along a track 110, by a pneumatic cylinder 111. A moving bracket 115 supports the fuel filler tube on the track. The distance the fuel filler tube is moved can be constant, and variations in the distance between the initial position of the fuel filler tube and the fuel inlet is accommodated by a bellows seal 112. Air pressure can be supplied to the fuel filler pneumatic cylinder by a fuel filler control air tube 116. Vapor displaced by inserted fuel is normally removed by a vapor recovery system. Displaced vapors can be removed from the fuel tank from by movement around the fuel inlet tube 109 into the bellow seal 112, and then removed through a conduit 113 to a vapor recovery system. Fuel can be supplied to the fuel filler tube 109 by a flexible fuel conduit 114, and through fuel cutoff valve 117.

Fuel filler tube 109 preferably has a pointed tip 118 to enable the tip to slip into a fuel cap orifice even if the fuel filler tube is not perfectly centered on the orifice.

After refueling is complete, the fuel filler tube can be retracted and then the source of vacuum to the suction cup can be discontinued, allowing the suction cup to release the hinged fuel inlet door. Discontinuation of this source of vacuum can cause the two pneumatic cylinders to revert to relaxed positions, thus disengaging from the refueling positions and allowing the vehicle being refueled to move.

Figure 2:
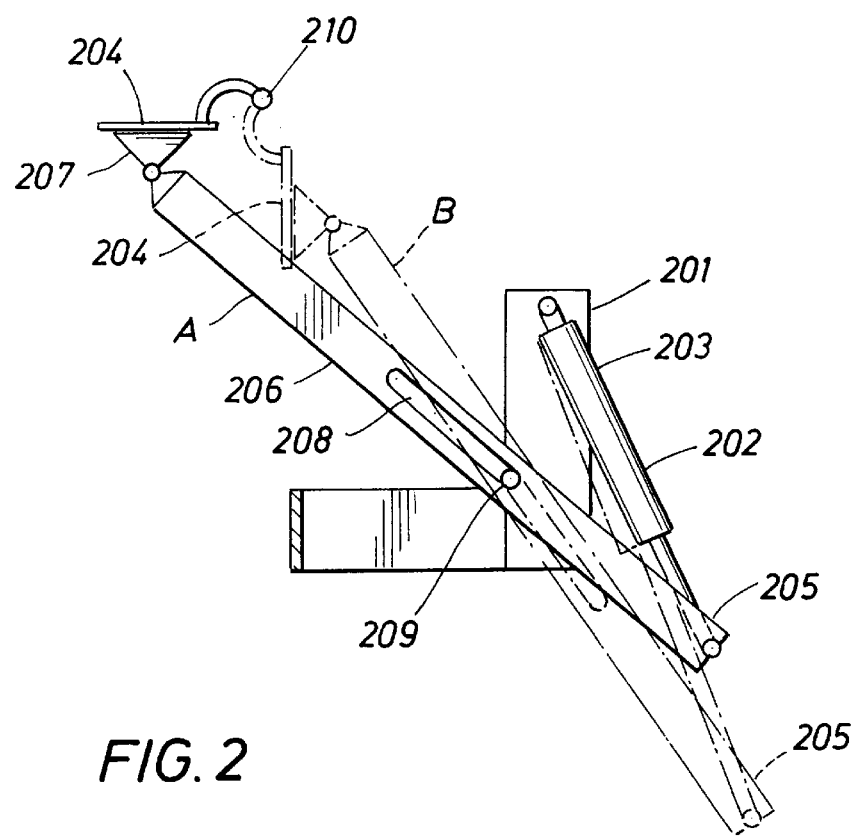
FIG. 2 is a top view of a mechanism to swing open a hinged fuel cap cover.

Referring now to FIG. 2, a top view of a mechanism to swing open a fuel inlet hinged door is shown. The mechanism is shown in two positions. Position A, in solid lines, with a hinged fuel inlet door 204 in a closed position, and Position B, shown in dashed lines, with the hinged fuel inlet cover door swung to an open position. A support bracket 201 provides a position to mount a pivoting end 203 of a pneumatic cylinder 202. The pneumatic cylinder is attached to at a moving end 205 to an arm 206 which serves to move open a fuel inlet cover. The arm is provided with a suction cup 207 at the end opposing the end attached to the pneumatic cylinder. The arm includes a slot 208 which allows lateral movement of the arm about a pin 209. The position of the arm can be urged toward the most forward position by, for example, a spring (not shown). As the pneumatic cylinder is extended, with the suction cup attached to a hinged fuel inlet cover, the suction cup pulls the cover around the axis of the inlet cover hinge 210.

Figure 3:
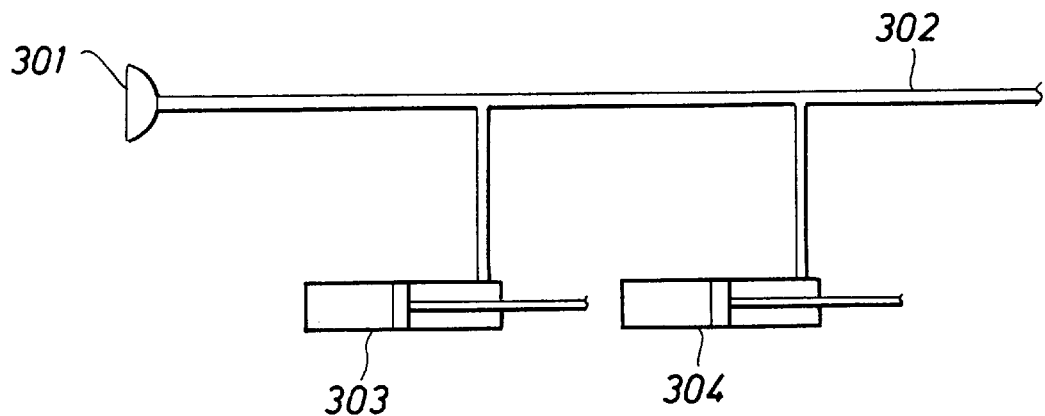
FIG. 3 is a schematic drawing of a pneumatic logic system of the present invention.

Referring now to FIG. 3, a schematic diagram of an acceptable pneumatic logic system for practice of the present invention is shown. A suction cup 301 is in communication with a source of vacuum (not shown) through a suction system 302. A pneumatic cylinder 303 effective to move an arm to swing open a hinged fuel cover door to which the suction cup is sealed. A second pneumatic cylinder 304 is provided which is effective to slide a fuel filler tube toward a vehicle's fuel inlet. The second pneumatic cylinder should not move significantly prior to the first pneumatic cylinder having essentially completed opening of the hinged door. This can be accomplished by biasing the second cylinder so that more vacuum is required to start moving the cylinder that the pressure effective to completely open the first cylinder. Alternatively, a restriction orifice could be provided in the suction system between the points where the vacuum supply to the two cylinders attach to the suction supply header, and the restriction orifice being effective to cause the first cylinder to essentially complete its movement prior to the second cylinder significantly moving.

Figure 4:
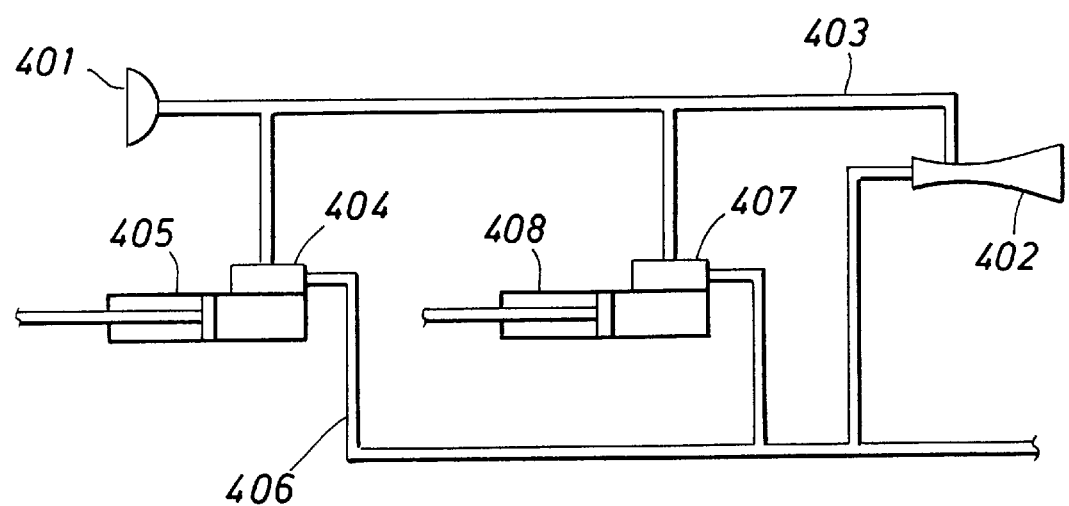
FIG. 4 is a schematic drawing of an alternative pneumatic logic system of the present invention.

Referring to FIG. 4, an alternative pneumatic logic system is shown. The system of FIG. 4 shows a positive pressure system with vacuum within the suction supply system triggering opening of poppet valves to cause movement of pneumatic cylinders of the present invention. A suction cup 401 has an inside which is in communication with a source of vacuum 402 (a venturi is shown) through a suction system 403. A first poppet valve 404 is provided to cause positive pressure air to actuate a first pneumatic cylinder 405. Positive air pressure is provided through an air supply system 406. A second poppet valve 407 is provided to supply air pressure to a second pneumatic cylinder 408. The poppet valves can be provided so that the first poppet valve opens at less of a vacuum than the second, and the pressure drawn down sufficiently slow in the vacuum supply system so than the system will cause hinged fuel inlet cover is opened prior to the fuel filler tube being moved forward along the track.

Figure 5A:
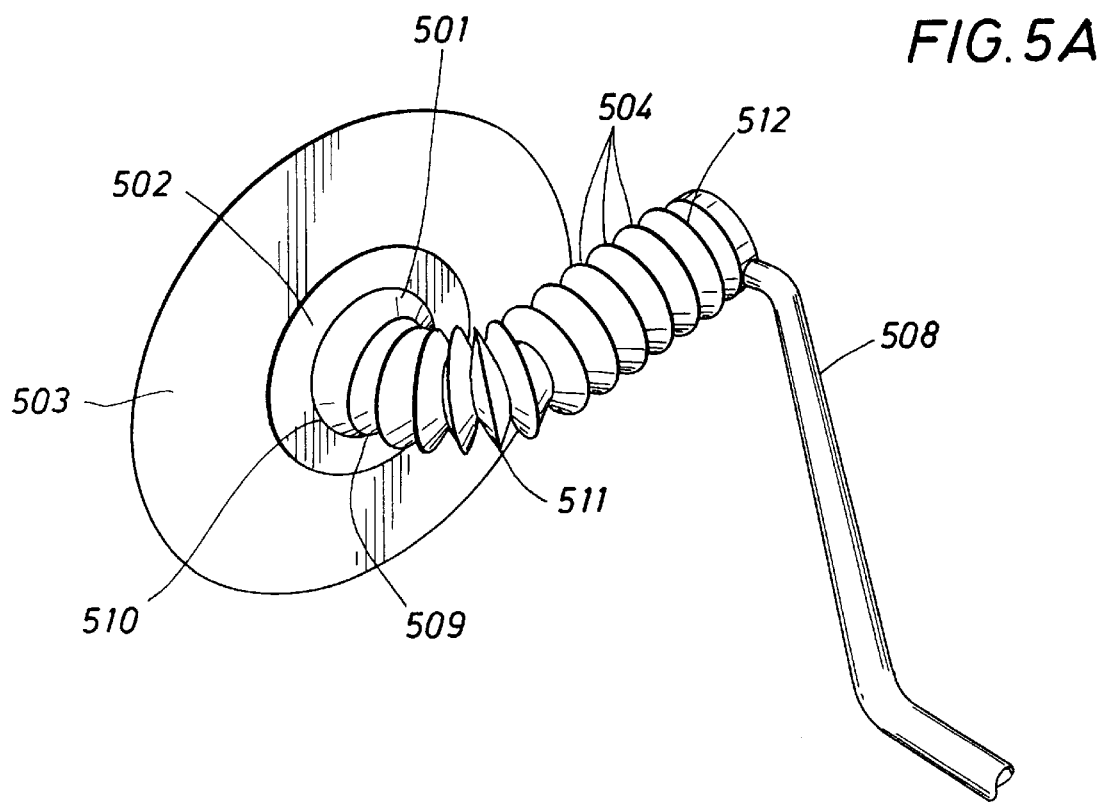
FIGS. 5A and 5B show schematically an alternative means to use a vacuum to swing open a hinged fuel inlet cover.
Figure 5B:
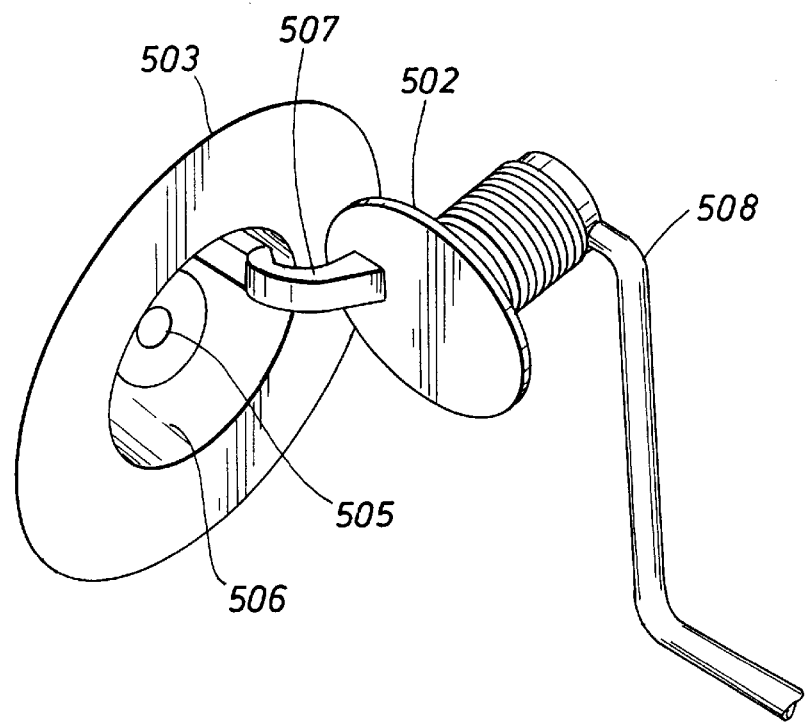

Referring now to FIGS. 5A and 5B, an alternative vacuum actuated means to swing open the hinged fuel cap cover is shown. The means to swing open the fuel inlet cover is shown secured by suction cup 501 to a hinged fuel inlet cover 502 on a vehicle 503. The suction cup is a J-shaped bellowed cup with a plurality of expandable bellows 504 connected so that in a relaxed state, the suction cup has a J shape, but in a contracted state, the bellows compact to a short cylinder. FIG. 5B shows the bellows in the compacted state, with the hinged fuel inlet cover pulled to an open position, exposing the fuel inlet nozzle 505, inside of the fuel inlet cavity 506, and the hinge 507. A single hollow arm 508 can support the suction cup, and application of vacuum to the suction cup can be provided through the hollow arm. The hollow arm can be moved forward with a vacuum being applied to the inside of the suction cup until the surface of the suction cup contacts the surface of the hinged fuel cover.

At this point, a vacuum will build within the suction cup. The existence of this vacuum preferably causes forward movement of the arm 508 to stop by way of a simple pneumatic logic system. The vacuum will also cause the suction cup to retract to a compacted state, and thereby pulling open the hinged fuel inlet cover. The arm supporting the suction cup requires only lateral movement, and no swinging movement to open the fuel inlet cover is required. This simplifies the apparatus, and thereby decreases cost and increases reliability of the system. The suction cup is effective to open the hinged fuel cap cover when a sealing surface of the suction cup is applied to the hinged fuel cap cover, and vacuum is applied to the inside of the suction cup. The suction cup in a relaxed state is in a J-shape, the J shape comprising a short leg 509, the short leg terminating on one end with a sealing ring 510 effective to seal against the fuel cap cover and at the other end terminating with an elbow 511, of about 90°, the elbow providing communication from inside the short leg to a longer leg 512, and the longer leg terminating with a source of vacuum, (in the embodiment of FIGS. 5A and 5B, the source of vacuum being the inside of the hollow arm 508), both legs and the elbow comprising of walls each comprising of a plurality of bellows. The suction cup has, in a contracted state, a shape of a short cylinder, the short leg, the elbow, and the long leg, in the contracted state being compressed into shorter segments each having essentially the same central axis, as shown in FIG. 5B. The suction cup being contracted by application of a vacuum on the inside volume of the suction cup. The suction cup is effective to pull open the fuel cap cover when a vacuum is applied to the inside of the suction cup when the suction cup is sealed onto the fuel cap cover and the long leg is, prior to contraction, extending in the direction of the hinge on the hinged fuel cap cover.

The system of the present invention is preferably utilized with an automated refueling system which includes utilization of a gas cap which has a spring-actuated opening in the cap to allow insertion of a fuel filler tube without removal of the gas cap. This is preferred because additional costs for a replacement gas cap are minimal, and the step of removal of the gas cap is eliminated, thus simplifying the system.

We claim:

1. A system for operating an automated refueling system, the system comprising:
    a source of vacuum:
    a suction cup, the suction cup being capable of mating with a hinged vehicle fuel cap cover and the suction cup having an inside which is in communication with the source of vacuum through a suction system;
    a vacuum actuated means to swing open the hinged fuel cap cover when a pressure within the suction system approaches the pressure of the source of vacuum; and
    a vacuum actuated cylinder to extend a filler tube insert into fuel tank inlet after the hinged fuel cap door is swung open.

2. The system of claim 1 wherein the suction cup is pivotably mounted on a vacuum actuated arm.

3. The system of claim 1 wherein the vacuum actuated arm to swing open the hinged fuel cap cover comprises a pneumatic cylinder powered by vacuum from the vacuum system.

4. The system of claim 1 wherein the vacuum actuated cylinder to extend the refueling filler tube comprises a pneumatic cylinder powered by vacuum from the vacuum system.

5. The system of claim 1 further comprising a poppet valve that is actuated by the vacuum system, and when actuated causes the vacuum actuated arm to swing open the hinged fuel cap cover by actuating a cylinder, the cylinder powered by a positive pressure fluid.

6. The system of claim 1 further comprising a poppet valve that is actuated by the vacuum system, and when actuated causes the vacuum actuated cylinder to extend the refueling filler tube by actuating a cylinder, the cylinder powered by a positive pressure fluid.

7. The system of claim 1 wherein the vacuum actuated means to swing open the hinged fuel cap cover comprises a J-shaped suction cup which in a relaxed state is in a J-shape, the J shape comprising a short leg, the short leg terminating on one end with a sealing ring effective to seal against the fuel cap cover and at the other end terminating with an elbow, of about 90°, the elbow providing communication from inside the short leg to a longer leg, and the longer leg terminating with a source of vacuum, both legs and the elbow comprising of walls each comprising of a plurality of bellows, the suction cup further having, in a contracted state, a shape of a short cylinder, the short leg, the elbow, and the long leg, in a contracted state being compressed into shorter segments each having essentially the same central axis, and the suction cup being contracted by application of a vacuum on the inside volume of the suction cup, and the suction cup is effective to pull open the fuel cap cover when a vacuum is applied to the inside of the suction cup when the suction cup is sealed onto the fuel cap cover and the long leg is, prior to contraction, extending in the direction of the hinge on the hinged fuel cap cover.

8. A suction cup for opening hinged covers, the suction cup comprising:
    a short leg, the short leg being hollow and comprising bellows;
    a sealing ring at one end of the short leg, the sealing ring effective to seal against a hinged cover when the sealing ring is placed against the cover;
    an elbow, the elbow being hollow and comprising radial bellows and connected to the short segment with the inside of the elbow and the inside of the short leg in communication with each other wherein the radial bellows, when relaxed result in the angle having an angle of about 90°, and when compressed by application of a vacuum to the inside of the elbow, results in the elbow being a short and straight shape;
    a long leg, the long leg being longer than the short leg, comprising bellows, being attached to the elbow at one end, being hollow and the inside, and the inside of the long leg being in communication with the elbow; and
    a connection to the second end of the long leg effective to provide communication between the inside of the long leg and a source of vacuum, wherein the suction cup in a relaxed state is in a J-shape, the J shape comprising the short leg, the longer leg, and the elbow, the suction cup further having, in a contracted state, a shape of a short cylinder, the short leg, the elbow, and the long leg, in a contracted state being compressed into shorter segments each having essentially the same central axis, and the suction cup being contracted by application of a vacuum on the inside volume of the suction cup, and the suction cup is effective to pull open the hinged cover when a vacuum is applied to the inside of the suction cup when the suction cup is sealed onto the hinged cover and the long leg is, prior to contraction, extending in the direction of the hinge on the hinged cover.

* * * * *